United States Patent [19]

Plepys et al.

[11] 4,154,767

[45] May 15, 1979

[54] FORMALDEHYDE-DIAROMATIC ETHER REACTION PRODUCTS

[75] Inventors: Raymond A. Plepys, Lake Jackson, Tex.; Edgar F. Hoy, Midland, Mich.

[73] Assignee: The Dow Chemical Company, Midland, Mich.

[21] Appl. No.: 775,135

[22] Filed: Mar. 7, 1977

Related U.S. Application Data

[63] Continuation-in-part of Ser. No. 595,939, Jul. 14, 1975, abandoned, which is a continuation-in-part of Ser. No. 378,459, Jul. 12, 1973, abandoned.

[51] Int. Cl.$^2$ .................... C07C 43/00; C07C 43/30
[52] U.S. Cl. .................... 260/609 F; 568/593; 568/636; 568/637; 568/638; 568/609; 252/64; 252/188.3 R; 528/109; 528/86; 528/110; 528/107
[58] Field of Search .................... 260/613 R, 609 F

[56] References Cited

U.S. PATENT DOCUMENTS 3,940,448   2/1976   Hoy .................... 260/613 R X

*Primary Examiner*—Bernard Helfin
*Attorney, Agent, or Firm*—B. G. Colley

[57] ABSTRACT

Reaction of the diphenyl ether with formaldehyde, an alcohol, water and acid catalyst produces a mixture of condensation products that can be cured to useful, thermally stable resins. These condensation products are also useful as functional fluids in capacitors and other electrical devices.

10 Claims, No Drawings

FORMALDEHYDE-DIAROMATIC ETHER REACTION PRODUCTS

CROSS REFERENCE TO RELATED APPLICATION

This application is a continuation-in-part of Ser. No. 595,939 filed July 14, 1975 which is a continuation-in-part of Ser. No. 378,459, filed July 12, 1973, both now abandoned.

BACKGROUND OF THE INVENTION

This invention relates to reaction products of formaldehyde, with diarly compounds such as diphenyl oxide, and to a process for their preparation.

It is known from Makromolekulare Chemie 97:163 (1966) and 107:196 (1967); British patent No. 942,057; and Ser. No. 236,472 filed Mar. 20, 1972, now abandoned, that resins can be prepared from formaldehyde and diphenyl oxide. However, the resins do not have methoxymethyl substituents.

It is also known from U.S. Pat. No. 3,342,873 that alkyloxymethyl diphenyl ethers can be prepared by chloromethylating diphenyl ether and then etherifying with lower alcohols. Recent toxicological studies have shown that bischloromethyl ether, used in the preparation of the above chloromethyl diphenyl ethers, may be carcinogenic. The present route of directly preparing similar methoxymethyl derivatives is advantageous as it avoids the intermediacy of chloromethyl ethers.

U.S. Pat. No. 3,940,448 discloses condensation products of naphthalene, formaldehyde, and aliphatic hydroxy hydrocarbon compounds.

SUMMARY OF THE INVENTION

The present invention is a cogeneric liquid formaldehyde diaromatic ether reaction product prepared by heating to a temperature in the range from about 50° to about 250° C. a mixture of (A) a diaryl compound selected from diphenyl oxide, diphenyl sulfide, their alkylated derivatives, their halogenated derivatives, or mixtures thereof,
(B) formaldehyde,
(C) water, and
(D) and aliphatic monohydroxy hydrocarbon compound having 0-3 ether oxygens, and not more than 4 carbon atoms between ether oxygens and at least one free hydroxyl group, in the presence of a catalytic amount of a strong acid catalyst wherein the amount of formaldehyde used ranges from about 1 to about 3 moles per mole of diaryl compound, the amount of water ranges from about 0.01 to about 2 moles per mole of diaryl compound and the amount of hydroxy hydrocarbon compound ranges from about 0.3 to about 10 moles per mole of diaryl compound.

The reaction products are useful in that they can be heated with strong acids and crosslinked to form films and to encapsulate electrical components. The reaction products are useful per se as nontoxic dielectric fluids for capacitors and the like.

DETAILED DESCRIPTION

The diaromatic ethers or diaryl ethers which can be reacted with formaldehyde to prepare the reaction products of this invention are diphenyl ether (diphenyl oxide) and diphenyl sulfide. Reaction products can also be prepared from the alkylated derivatives of the foregoing wherein one or both aromatic ring are substituted by one or two alkyl groups of 1-10 carbon atoms each.

If desired, the diaromatic ethers can be halogenated in one or both rings with fluorine, chlorine, bromine, or iodine groups. Mixtures of the foregoing are also useful in this invention.

The above diaromatic ethers are mixed and reacted with about 1 to about 3 moles of formaldehyde at a temperature range from 50° to about 250° C. in the presence of about 0.01 to about 2 moles of water per mole of diaryl ether and in the presence of about 0.3 to about 10 moles of an aliphatic monohydroxy hydrocarbon compound having 0-3 ethers oxygens.

The presence of water in the ranges recited above is essential to this invention since the use of amounts below this range results in very low yields of the desired reaction product while amounts greater than this amount result in greatly increased reaction times.

The above reaction proceeds readily in the presence of a catalytic amount of a strong acid catalyst. For the purposes of this invention a catayltic amount is defined as about 1 to about 20 mol percent of the strong acid based on the diaryl ether.

Examples of strong acid catalysts are sulfuric acid, phosphoric acid, p-toluene sulfonic acid, perchloric acid, diphenyl oxide sulfonic acid, strong acid cation exchange resins and the like.

A commercial mixture of formaldehyde, methanol and water sold under the trade name Methyl Formcel ® is a convenient source of the above formaldehyde and at least a portion of the methanol reactants. Another useful reactant is methylal supplying the formaldehyde and alcohol.

Examples of the above aliphatic monohydroxy hydrocarbon compounds are: monohydric alcohols of 1-12 carbon such as methanol, ethanol, propanol, butanol, 2-ethyl hexanol and the like; monoalkyl ethers of glycols of 3-12 carbons such as ethylene glycol monomethyl ether, ethylene glycol monoethyl ether, 1,2-propylene glycol monomethyl ether, ethylene glycol monobutyl ether, and the like; and monoalkylethers of polyglycols of 5-12 carbons such as diethylene glycol monomethyl ether, diethylene glycol monoethyl ether, diethylene glycol monobutyl ether, triethylene glycol monoethyl ether, triethylene glycol monobutyl ether, and the like.

The following examples are presented to illustrate but not limit the invention.

EXAMPLE 1

An acid resistant pressure vessel equipped with paddle stirrer and thermowell was charged with 300 g. diphenyl oxide, 300 g. Methyl Formcel ® (approx. 55% formaldehyde, 11% water, 34% methanol) and 20 g. 98% sulfuric acid. The mixture was heated with stirring at 145° for 3.5 hours and cooled. A minor, top aqueous layer was decanted and the organic layer was washed with water, dilute caustic, dried over anhydrous magnesium sulfate and evaporated leaving 375.5 g. of a light tan oil. Analysis by vapor phase chromatography showed about 5% unreacted diphenyl oxide. The remainder was higher molecular weight species. The average molecular weight as determined by gel permeation chromatography was approximately 550 ranging from 170 to 1250. Analysis by nuclear magnetic resonance (nmr) showed the following relative areas:

| | |
|---|---|
| aromatic hydrogens | 140 |
| (CH₂O)ₓ hydrogens | 54 |
| -Ar-Ch₂-Ar-hydrogens | 9 |
| (OCH₃)ₓ hydrogens | 40 |

EXAMPLE 2

A similar reactor was charged with 170 g. (1 mole) diphenyl oxide, 165 g. (3 moles formaldehyde) Methyl Formcel ® and 24 g. (0.2 mole) 85% phosphoric acid. The mixture was heated at 150° for 3.5 hours and worked up as in the previous example. The residue showed 41% unreacted diphenyl oxide by vapor phase chromatography and an average product molecular weight of about 250.

EXAMPLE 3

A 1-liter acid resistant metal pressure vessel equipped with paddle stirrer and thermowell was charged with 207 g. diphenyl oxide (1.2 moles) 207 g. Methyl Formcel ® (55% fromaldehyde) and 42 g. (0.244 mole) p-toluenesulfonic acid. The mixture was heated with stirring for 3 hours 45 minutes at 140° C. Upon cooling the vessel contents were found to be a white, homogenized, thick slurry which did not settle. A small representative portion was treated by dissolving in $CH_2CL_2$, washing with water and dilute caustic. Drying and evaporation left a clear, thick resin which showed no diphenyl oxide on vapor phase chromatography. The average molecular weight by gel permeation chromatography was about 1,700. Nmr analysis showed 1.2 ($CH_2O$) groups per diphenyl oxide unit and 0.77 $ArCH_2Ar$ groups per diphenyl oxide unit. There were two $CH_2O$ groups per $OCH_3$.

EXAMPLE 4

An acid resistant (Hastelloy C) pressure vessel equipped with an agitator was charged with 340 g. (2 moles) diphenyl oxide, 220 g. Methyl Formcel ® (4 moles formaldehyde) and 40 g. Dowex ® MSC-1 sulfonated macroreticular resin (acid form). The mixture was heated with stirring at 155° C. for 4.5 hours. After cooling, the resin was filtered off and the filtrate was taken up in methylene chloride. After washing with water and drying the methylene chloride was evaporated. Analysis by gel permeation and vapor phase chromatography showed 56% unreacted diphenyl oxide. The average molecular weight of the resin was about 250 which corresponds to substitution of $(CH_2O)_{1-3} CH_3$ on diphenyl oxide.

A 302 g. sample of this material was vacuum distilled without a column at 0.7 to 1.5 mm Hg pressure to give 165 g. of diphenyl oxide in the distillate and a residual resin of 120 g.

EXAMPLE 5

A 1-liter Hastelloy C pressure vessel was charged with 170 g. (1 mole) diphenyl oxide, 90 g. (3 moles) formaldehyde as paraformaldehyde, 222 g. (3 moles) 1-butanol, 19 g. $H_2SO_4$ (0.19 mole) and 50 g. (2.7 moles) water. The mixture was heated at 152° C. for 5.5 hours, cooled, and diluted with 200 ml. methylene chloride and 100 ml. water. The organic layer was separated and the methylene chloride was removed under vacuum. The remaining butanol was removed at 100 mm Hg pressure. The major portion of unreacted diphenyl oxide was removed at a pot temperature of 185° C. at 1.5 mm Hg. This left 119 g. of resin which showed about 20% diphenyl oxide by gel permeation chromatography and major constituents at approximate molecular weights of 290, 320, and 445.

EXAMPLE 6

A 1-liter Hastelloy C pressure vessel was charged with 85 g. (0.5 mole) diphenyl oxide, 244 g. (1.5 moles) diethylene glycol monobutyl ether, 48 g. (1.5 moles) formaldehyde as paraformaldehyde, 7.5 g. water (0.42 mole) and 3 g. (0.03 mole) sulfuric acid. The mixture was heated with stirring for 6 hours at 150° C. After cooling the product was diluted with 100 ml. water and 200 ml. of $CH_2CL_2$. The organic layer was separated and washed successively with 10% NaOH and water. The solvents and unreacted materials were stripped off with a final pot temperature of 165° C. and a pressure of 2 mm Hg. This left a resin of 21.5 g. which, by gel permeation chromatography, showed about 27% diphenyl oxide and 16% diethylene glycol monobutyl ether formal. There were also major peaks at approximate molecular weights of 400 (25%), 460 (19%), 580 (8%) and 1200 (5%). The 400 mw peak corresponds to diphenyl oxide substituted with $-CH_2OCH_2R$ where R is the diethylene glycol monobutyl ether moiety ($-O-CH_2CH_2-O-CH_2CH_2-O-CH_2CH_2CH_2CH_3$).

EXAMPLE 7

The procedure of Example 6 is repeated using 0.5 mole of diphenyl sulfide. Substantially the same results are obtained.

EXAMPLE 8

An acid resistant pressure vessel equipped with a paddle-stirrer and thermowell was charged with 285 gms diphenyl oxide, 103 gms methanol, 54 gms 91% paraformaldehyde, 30 gms water and 33 gms 98% sulfuric acid. The mixture was heated with stirring at 137° C. for 4.0 hours then cooled. The top organic layer which formed was separated and neutralized of residual acidity using a basic anion exchange resin. The unreacted diphenyl oxide, 114 gms, was distilled at reduced pressure leaving 230 gms of a clear, yellow oil. Analysis was by quantitative vapor phase chromatography employing internal standard methods in which the analytical sample is dissolved in dichloromethane. The analysis was as follows, in order of their appearance from the VPC:

| | Wt. % |
|---|---|
| 3 unknowns | 0.131 |
| diphenyloxide (DPO) | 0.259 |
| methyl DPO | 0.021 |
| o-methoxymethyl DPO | 9.897 |
| p-methoxymethyl DPO | 40.634 |
| hydroxymethyl DPO | 1.275 |
| o-methoxymethoxymethyl DPO | 1.150 |
| 1 unknown | 0.13 |
| p-methoxymethoxymethyl DPO | 3.1403 |
| o,o-di(methoxymethyl) DPO | 1.807 |
| o,p-di(methoxymethyl) DPO | 3.873 |
| 1 unknown | 0.55 |
| p,p-di(methoxymethyl) DPO | 6.198 |
| 4 unknowns | 1.962 |
| tri(methoxymethyl) DPO isomers | 2.538 |
| 7 unknowns (max 0.6561) | 2.533 |
| o-bis(phenoxyphenyl) methane | 1.1414 |
| 1 unknown | 0.3052 |
| p-bis(phenoxyphenyl) methane | 8.6548 |
| 4 unknowns | 1.0498 |

| | Wt. % |
|---|---|
| methoxymethylbis(phenoxyphenyl methane) isomers | 5.3436 |
| 4 unknowns | 1.1201 |

The average methoxy equivalent weight of the cogeneric reaction product was about 233 and about 75% of the product was methoxy functional.

EXAMPLE 9

The procedure of Example 8 was followed except that the reactants were 170 gms of diphenyl oxide, 76.6 grams of methylal, 20 grams sulfuric acid, and 36 grams of water. The reactor was heated to 144° C. for four hours, then cooled. The organic layer was then separated, water washed, and stripped to remove residual formaldehyde, methanol and water. Vapor phase chromatographic analysis showed substantially the same results as in Example 8.

We claim:

1. The cogeneric liquid formaldehyde-diaromatic ether reaction product produced by heating to a temperature in the range from about 50° to about 250° C. a mixture of
   (A) a diaryl compound selected from diphenyl oxide, diphenyl sulfide, their alkylated derivatives, their halogenated derivatives, or mixtures thereof,
   (B) formaldehyde,
   (C) water, and
   (D) an aliphatic monohydroxy hydrocarbon compound having 0-3 ether oxygens, and not more than 4 carbon atoms between ether oxygens and at least one free hydroxyl group,
in the presence of a catalytic amount of a strong acid catalyst wherein the amount of formaldehyde used ranges from about 1 to about 3 moles per mole of diaryl compound, the amount of water ranges from about 0.01 to about 2 moles per mole of diaryl compound and the amount of hydroxy hydrocarbon compound ranges from about 0.3 to about 10 moles per mole of diaryl compound.

2. The product as set forth in claim 1 wherein the monohydroxy hydrocarbon compound is selected from aliphatic monohydric alcohols of 1-12 carbons, monoalkyl ethers of polyglycols of 5-12 carbons, and monoalkyl ethers of glycols of 3-12 carbons.

3. The product as set forth in claim 1 wherein the diaryl compound is diphenyl oxide.

4. The product as set forth in claim 1 wherein the diaryl compound is diphenyl sulfide.

5. The cogeneric liquid formaldehyde-diaromatic ether reaction product produced by heating to a temperature in the range from about 50° to about 250° C. a mixture of
   (A) a diaryl compound selected from diphenyl oxide, diphenyl sulfide, their alkylated derivatives, their halogenated derivatives, or mixtures thereof, wherein the alkyl group has up to 10 carbon atoms and each aromatic ring may be substituted by up to a maximum of two halogen atoms or alkyl groups,
   (B) formaldehyde,
   (C) water, and
   (D) an aliphatic monohydroxy hydrocarbon compound selected from alkanols of 1-12 carbons, monoalkyl ethers of polyethylene glycols of 5-12 carbons, and monoalkyl ethers of glycols of 3-12 carbons, in the presence of a catalytic amount of a strong acid catalyst wherein the amount of formaldehyde ranges from about 1 to about 3 moles per mole of diaryl compound, the amount of water ranges from about 0.01 to about 2 moles per mole of diaryl compound and the amount of monohydroxy hydrocarbon compound ranges from about 0.3 to about 10 moles per mole of diaryl compound.

6. The product of claim 5 wherein the diaryl compound is diphenyl oxide.

7. The product of claim 5 wherein the diaryl compound is diphenyl sulfide.

8. The product of claim 6 wherein the monohydroxy hydrocarbon compound is methanol.

9. The product of claim 6 wherein at least a part of the monohydroxy hydrocarbon compound, the formaldehyde and water, are supplied by employing a solution of formaldehyde, methanol and water.

10. The product of claim 6 wherein at least a part of the monohydroxy hydrocarbon compound, the formaldehyde and water, are supplied by employing methylal.

UNITED STATES PATENT AND TRADEMARK OFFICE
CERTIFICATE OF CORRECTION

PATENT NO. : 4,154,767

DATED : May 15, 1979

INVENTOR(S) : Raymond A. Plepys and Edgar F. Hoy

It is certified that error appears in the above-identified patent and that said Letters Patent are hereby corrected as shown below:

Column 1, line 14; change "diarly" to --diaryl--.

Column 1, line 45; change "and" to --an--.

Column 2, line 9; insert --about-- between "from" and "50°".

Column 2, line 21; change "catayltic" to --catalytic--.

Column 2, line 61; change "375.5" to --378.5--.

Column 3, line 22; change "fromaldehyde" to --formaldehyde--.

Signed and Sealed this

Second Day of October 1979

[SEAL]

Attest:

RUTH C. MASON
Attesting Officer

LUTRELLE F. PARKER
Acting Commissioner of Patents and Trademarks